(12) United States Patent
Kim et al.

(10) Patent No.: US 9,482,606 B2
(45) Date of Patent: Nov. 1, 2016

(54) METHOD FOR PROCESSING DATA AND ELECTRONIC DEVICE THEREOF

(71) Applicant: Samsung Electronics Co., Ltd., Gyeonggi-do (KR)

(72) Inventors: Jae-Yub Kim, Gyeonggi-do (KR); Do-Hyoung Chung, Seoul (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 32 days.

(21) Appl. No.: 14/529,903

(22) Filed: Oct. 31, 2014

(65) Prior Publication Data
US 2015/0123984 A1 May 7, 2015

(30) Foreign Application Priority Data
Nov. 1, 2013 (KR) .................. 10-2013-0132503

(51) Int. Cl.
G09G 5/02 (2006.01)
G01N 19/10 (2006.01)
G01K 1/20 (2006.01)
G01D 3/036 (2006.01)
H04M 1/725 (2006.01)

(52) U.S. Cl.
CPC .............. *G01N 19/10* (2013.01); *G01K 1/20* (2013.01); *G01D 3/0365* (2013.01); *H04M 1/72544* (2013.01); *H04M 2250/12* (2013.01)

(58) Field of Classification Search
None
See application file for complete search history.

(56) References Cited

U.S. PATENT DOCUMENTS

| 2007/0027580 | A1* | 2/2007 | Ligtenberg | G05D 23/19 700/300 |
| 2012/0326834 | A1* | 12/2012 | Kennedy | H04M 1/72519 340/3.1 |
| 2013/0099008 | A1 | 4/2013 | Aljabari et al. | |
| 2013/0249932 | A1* | 9/2013 | Siotis | G09G 3/20 345/589 |
| 2014/0311209 | A1* | 10/2014 | Niederberger | G01K 15/007 73/1.06 |
| 2014/0355649 | A1* | 12/2014 | Niederberger | G01D 3/0365 374/152 |
| 2015/0073741 | A1* | 3/2015 | Wuest | G01D 3/032 702/104 |

* cited by examiner

*Primary Examiner* — Xiao Wu
*Assistant Examiner* — Mohammad H Akhavannik
(74) *Attorney, Agent, or Firm* — Cha & Reiter, LLC.

(57) ABSTRACT

A method for operating an electronic device including a first sensor is provided, the method including: obtaining a first reading from the first sensor; detecting a state of the electronic device; and adjusting the first reading based on the state the electronic device to generate an adjusted reading; and performing, by the electronic device, an action based on the adjusted reading; wherein the first sensor includes at least one of a temperature sensor and a humidity sensor.

18 Claims, 13 Drawing Sheets

| FF33FF | FF00FF | 66FFFF | 66CCFF | 6699FF | 6666FF | 6633FF |
|--------|--------|--------|--------|--------|--------|--------|
| FF33CC | FF00CC | 66FFCC | 66CCCC | 6699CC | 6666CC | 6633CC |
| FF3399 | FF0099 | 66FF99 | 66CC99 | 669999 | 666699 | 663399 |
| FF3366 | FF0066 | 66FF66 | 66CC66 | 669966 | 666666 | 663366 |
| FF3333 | FF0033 | 66FF33 | 66CC33 | 669933 | 666633 | 663333 |
| FF3300 | FF0000 | 66FF00 | 66CC00 | 669900 | 666600 | 663300 |
| FF33FF | FF00FF | 33FFFF | 33CCFF | 6699FF | 3366FF | 3333FF |
| CC33CC | CC00CC | 33FFCC | 33CCCC | 3399CC | 3366CC | 333CCC |
| CC3399 | CC0099 | 33FF99 | 33CC99 | 339999 | 336699 | 333399 |
| CC3366 | CC0066 | 33FF66 | 33CC66 | 339966 | 336666 | 333366 |
| CC3333 | CC0033 | 33FF33 | 33CC33 | 339933 | 336633 | 333333 |
| CC3300 | CC0303 | 33FF00 | 33CC00 | 339900 | 336600 | 333000 |
| 9933FF | 9900FF | 00FFFF | 00CCFF | 0099FF | 0066FF | 0033FF |
| 9933CC | 9900CC | 00FFCC | 00CCCC | 0099CC | 0066CC | 0033CC |
| 993399 | 990099 | 00FF99 | 00CC99 | 009999 | 006699 | 003399 |
| 993366 | 990066 | 00FF66 | 00CC66 | 009966 | 006666 | 003366 |
| 993333 | 990033 | 00FF33 | 00CC33 | 009933 | 006633 | 003333 |
| 993300 | 990000 | 00FF00 | 00CC00 | 009900 | 006600 | 003300 |

~501

METHOD FOR PROCESSING DATA AND ELECTRONIC DEVICE THEREOF

CLAIM OF PRIORITY

This application claims the benefit under 35 U.S.C. §119 (a) of a Korean patent application filed in the Korean Intellectual Property Office on Nov. 1, 2013 and assigned Serial No. 10-2013-0132503, the entire disclosure of which is hereby incorporated by reference.

BACKGROUND

1. Technical Field

The present disclosure relates to electronic devices, and more particularly to a method and apparatus for processing data.

2. Description of the Related Art

As a mobile communication technology develops, an electronic device is used as an essential communication device of an individual. Furthermore, as an electronic device provides not only a voice communication function but also various additional services such as a camera, data communication, moving picture reproduction, audio reproduction and a messenger, schedule management, an alarm function, etc., various programs that may use these functions, and a user may perform an input to the electronic device via various input methods or using various objects.

An electronic device may calculate actual temperature based on temperature/humidity information before correction, measured by a temperature/humidity sensor. That is, a smartphone may represent temperature of a temperature/humidity sensor mounted thereon as if it were actual temperature. However, since temperature/humidity information before correction is much influenced by other parts inside the smartphone, a difference between measured temperature and actual temperature may occur. Therefore, a smartphone may apply a temperature compensation engine to measured values of a thermistor inside a Printed Circuit Board (PCB), and show temperature/humidity results that approach actual temperature/humidity.

SUMMARY

According to one aspect of the disclosure, a method for operating an electronic device is provided including a first sensor, the method comprising: obtaining a first reading from the first sensor; detecting a state of the electronic device; adjusting the first reading based on the state the electronic device to generate an adjusted reading; and performing, by the electronic device, an action based on the adjusted reading; wherein the first sensor includes at least one of a temperature sensor and a humidity sensor.

According to another aspect of the disclosure, an electronic device is provided comprising a first sensor and a processing circuitry configured to: obtain a first reading from the first sensor; detect a state of the electronic device; and adjust the first reading based on the state the electronic device to generate an adjusted reading; and perform, by the electronic device, an action based on the adjusted reading; wherein the first sensor includes at least one of a temperature sensor and a humidity sensor.

BRIEF DESCRIPTION OF THE DRAWINGS

The above and other aspects, features and advantages of certain aspects of the present disclosure will be more apparent from the following description taken in conjunction with the accompanying drawings in which.

Throughout the drawings, like reference numerals will be understood to refer to like parts, components and structures.

DETAILED DESCRIPTION

Figure 1:
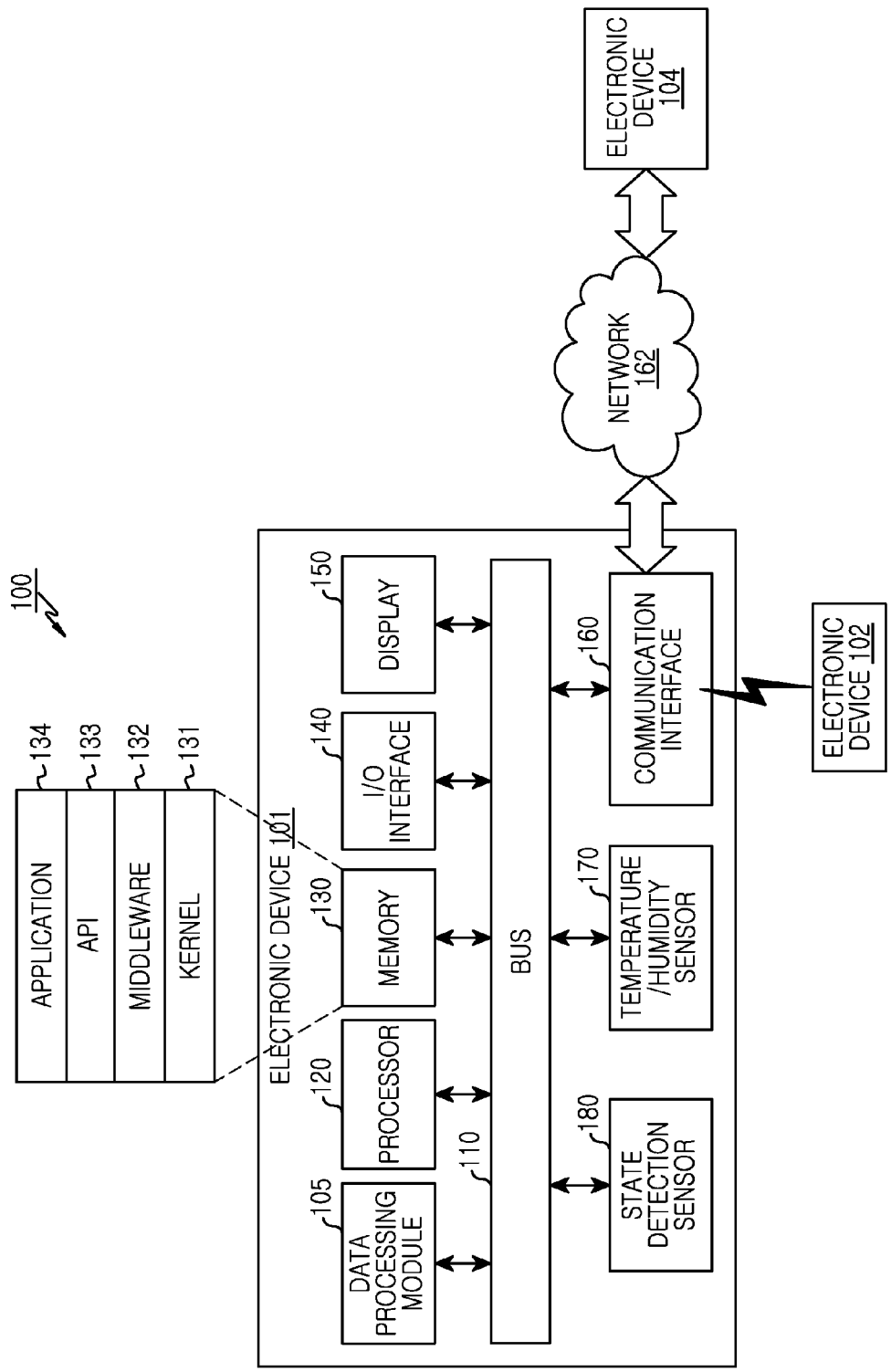
FIG. 1 is a block diagram of an example of an electronic device 101 according to various aspects.

An electronic device may set various circumstances depending on a state where the electronic device is positioned in order to correct (or reset) an error of one or more sensors connected to the electronic device caused by interferences of one or more parts included inside or outside the electronic device. The electronic device may include one or more correction engines that may correct a value obtained by a sensor of the electronic device based on one or more variables measured for a designated circumstance.

An electronic device according to the present disclosure may y include a smartphone, a tablet personal computer (PC), a mobile phone, a video phone, an e-book reader, a desktop PC, a laptop PC, a netbook computer, a Personal Digital Assistant (PDA), a Portable Multimedia Player (PMP), an MP3 player, a mobile medical device, a camera, and a wearable device (e.g., at least one of a head-mounted-device (HMD) such as an electronic glasses, electronic clothes, an electronic bracket, an electronic necklace, an electronic appcessory, or a smartwatch). Additionally or alternatively, the electronic device may be a smart home appliance having a communication function. The smart home appliance may include, for example, at least one of a television, a Digital Video Disk (DVD) player, an audio, a refrigerator, an air conditioner, a cleaner, an oven, an electronic range, a washing machine, an air purifier, a set-top box, a TV box (for example, Samsung HomeSync™, Apple TV™, or Google TV™), game consoles, an electronic dictionary, an electronic key, a camcorder, or an electronic frame. Additionally or alternatively, the electronic device may include at least one of various medical devices (e.g., Magnetic Resonance Angiography (MRA), Magnetic Resonance Imaging (MRI), Computed Tomography (CT), a shooting device, an ultrasonic device, etc.), a navigation device, a Global Positioning System (GPS) receiver, an event data recorder (EDR), a flight data recorder (FDR), an automobile infotainment device, electronic equipment for a ship (e.g., a navigation device for a ship, a gyro compass, etc.), an avionics, or a security device.

Additionally or alternatively, the electronic device may include at least one of a furniture or a portion of a building/structure including a communication function, an electronic board, an electronic signature receiving device, a projector, or various measurement devices (e.g., waterworks, electricity, gas, or radio waves, etc.). An electronic device according to the present disclosure may be a combination of one or more of the above-described devices. Also, it is obvious to a person of ordinary skill in the art that the electronic device according to the present disclosure is not limited to the above-described devices. Hereinafter, an electronic device according to various aspects is described with reference to the accompanying drawings. A terminology of a user used in various aspects may include and indicate a person who uses an electronic device or a device (e.g., an artificial intelligence electronic device) that uses the electronic device.

FIG. 1 is a block diagram 100 illustrating an electronic device 101 according to various aspects.

Referring to FIG. 1, the electronic device 101 may include a data processing module 105, a bus 110, a processor 120, a memory 130, an input/output (I/O) interface 140, a display module 150, a communication interface 160, a temperature/humidity sensor 170, or a state detection sensor 180.

The data processing module 105 may include any suitable type of processing circuitry, such as a processor (e.g., an ARM-based processor, a MIPS-based processor, an x86-based processor, etc.), a Field-Programmable Gate Array (FPGA), or an Application-Specific Integrated Circuit (ASIC). The data processing module 105 may correct temperature/humidity information obtained by the temperature/humidity sensor 170 with reference to context awareness obtained by the state detection sensor 180 of the electronic device 101. The data processing module 105 may determine one or more correction engines included in a database that matches context awareness of the electronic device 101. The data processing module 105 may correct temperature/humidity information obtained by the temperature/humidity sensor 170 of the electronic device using a correction engine designated in a determined correction engine. The data processing module 105 may display all or a portion of information regarding an operation of correcting the above-described temperature/humidity information on the display module 150. Although the data processing module 105 and the processor 110 are depicted as separate components, it will be clear that in some implementations they can be integrated together.

The bus 110 may be a circuit for connecting the above-described elements with each other, and transferring communication (e.g., a control message) between the above-described elements.

The processor 120 may include any suitable type of processing circuitry, such as a processor (e.g., an ARM-based processor, a MIPS-based processor, an x86-based processor, etc.), a Field-Programmable Gate Array (FPGA), or an Application-Specific Integrated Circuit (ASIC). The processor 120 may receive, for example, an instruction from above-described other elements (e.g., the memory 130, the I/O interface 140, the display module 150, the communication interface 160, etc.) via the bus 110, decipher the received instruction, and execute an operation or a data processing corresponding to the deciphered instruction.

The memory 130 (e.g., the memory 130) may store an instruction or data received from the processor 120 or other elements (e.g., the I/O interface 140, the display module 150, the communication interface 160, etc.) or generated by the processor 120 or other elements. The memory 130 may include, for example, programming modules such as a kernel 131, a middleware 132, an Application Programming Interface (API) 133, or an application 134, etc. The above-described programming modules may be configured using a software, a firmware, a hardware, or a combination of two or more of these.

The kernel 131 may control or manage system resources (e.g., the bus 110, the processor 120, or the memory 130, etc.) used for executing an operation or a function implemented in the rest of the programming modules, for example, the middleware 132, the API 133, or the application 134. Also, the kernel 131 may provide an interface that allows the middleware 132, the API 133, or the application 134 to access an individual element of the electronic device 101 and control or manage the same.

The middleware 132 may perform a mediation role so that the API 133 or the application 134 may communicate with the kernel 131 to give and take data. Also, in relation to task requests received from the (plurality of) applications 134, the middleware 132 may perform load balancing for a task request using a method of assigning a priority that may use a system resource (e.g., the bus 110, the processor 120, or the memory 130, etc.) of the electronic device 101 to at least one of the (plurality of) applications 134.

The API 133 is an interface that allows the application 134 to control a function provided by the kernel 131 or the middleware 132, and may include, for example, at least one interface or function for file control, window control, image processing, or character control, etc.

The I/O interface 140 may receive, for example, an instruction or data from a user and transfer the same to the processor 120 or the memory 130 via the bus 110. The display module 150 may display an image, a video, or data, etc. to the user. According to an aspect, in the case where the display module 150 is provided in the form of a touchscreen panel, the user may input an instruction via a gesture of touching or hovering (e.g., indirect touch input) the display module 150.

The communication interface 160 may connect communication between the electronic device 101 and an auxiliary electronic device or an electronic device 104 or a server 164. The communication interface 160 may support a predetermined short distance communication protocol (e.g., Wireless Fidelity (Wi-Fi), Bluetooth (BT), Near Field Communication (NFC)), or predetermined network communication 162 (e.g., the Internet, a Local Area Network (LAN), a Wide Area Network (WAN), a telecommunication network, a cellular network, a satellite network, or a Plain Old Telephone Service (POTS), etc.). Each of the electronic devices 102 and 104 may the same (e.g., the same type) device as the electronic device 101 or a different (e.g., a different type) device.

The temperature/humidity sensor 170 may be attached to the interior and/or exterior of the electronic device 101 to determine temperature and/or humidity (referred to as temperature/humidity hereinafter) of devices, ambient temperature/humidity of the electronic device 101. For example, the temperature/humidity sensor 170 may be attached close to an earphone terminal (not shown) that may be directly influenced by outside temperature and/or humidity of the electronic device 100.

The temperature/humidity sensor 170 may be attached close to a heat emitting source such as the processor 120 and/or peripherals (a display unit, a camera, a charging module, a wiring of a PCB) of the electronic device 101 to measure temperature/humidity of the heat emitting source or the vicinity of the heat emitting source. In addition, the temperature sensor 170 may additionally include one or more temperature sensors 170 at a position that may measure temperature of the interior of the electronic device 101 without a direct influence from the heat emitting source of the electronic device 101. The electronic device 101 may include one or more temperature sensors 170 that obtain temperature/humidity of the inside/outside of the electronic device 101, the processor 120 or peripherals of the electronic device. According to various aspects, temperature/humidity information is temperature and/or humidity information, and may mean temperature information and humidity information, respectively, and mean both temperature information and humidity information.

The state detection sensor 180 may be one or more sensors that may obtain context awareness of the electronic device 101, and may be a sensor module including two or more sensors. The state detection sensor 180 may obtain information such as a 3-dimensional coordinate, a slope of the electronic device, movement, a moving direction of the electronic device 101, and a state where the electronic device 101 is positioned via sensors such as an acceleration sensor, a slope sensor, a gyroscope, a geomagnetic sensor, a GPS, an luminance sensor a proximity sensor, luminance sensora pupil (one's eye) detection sensor that may obtain information regarding a state of the electronic device 101, a brainwave sensor, and/or any other suitable type of sensor.

Figure 2:
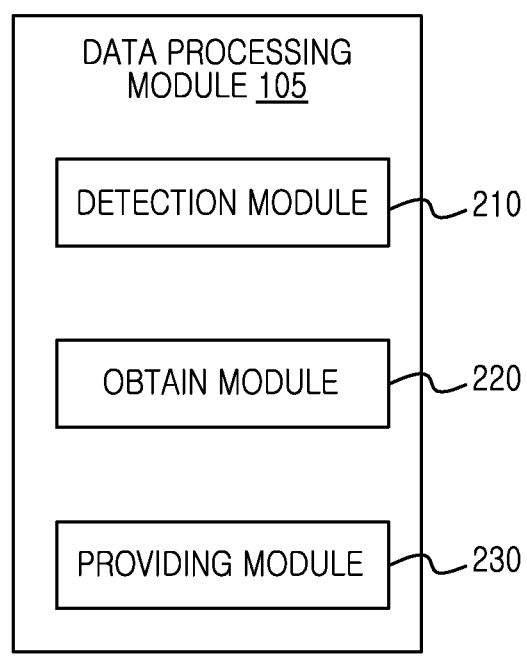
FIG. 2 is a block diagram illustrating a data processing module 105 in an electronic device according to various aspects.

FIG. 2 is a block diagram illustrating a data processing module 105 in an electronic device according to various aspects.

Referring to FIG. 2, the data processing module 105 may include at least one of a detection module 210, an obtain module 220, and a providing module 230. Each module described below may include hardware configured to perform a described operation and/or a combination of hardware and software.

The detection module 210 may detect a designated input of the electronic device 101 and control the temperature/humidity sensor 170 to obtain temperature information and/or humidity information of the interior and/or exterior of the electronic device. The detection module 210 may detect a designated input of the electronic device 101 and control the state detection sensor 180 to obtain context awareness of the electronic device 101.

The obtain module 220 may determine a correction engine stored in a database that matches at least one of state information obtained by the state detection module 180 of the electronic device 101. The obtain module 220 may apply a correction engine designated in a correction engine and correct temperature/humidity information obtained by the temperature/humidity sensor 170.

The providing module 230 may output through the output device such as a display or a speaker at least one of a correction engine determined using context awareness of the electronic device 101, temperature/humidity information obtained by the temperature/humidity sensor 170, a correction process, a correction state, and corrected temperature/humidity information.

According to various aspects, the electronic device may include a memory including one or more correction values, one or more temperature/humidity sensors for obtaining temperature information and humidity information of the outside of the electronic device, one or more state detection sensors for obtaining context awareness of the electronic device, a data processing module 105 for obtaining at least one of the temperature information and the humidity information of the outside of the electronic device, obtaining the context awareness of the electronic device, determining a correction value for at least one of the temperature information and the humidity information based on the context awareness, and correcting at least one of the temperature information and the humidity information depending on the correction value, and one or more processors (e.g., the processor 120) for controlling the data processing module 105.

According to various aspects, the data processing module 105 may obtain the context awareness using at least one of the acceleration sensor, the slope sensor, the gyroscope, the geomagnetic sensor, the GPS, the luminance sensor, the proximity sensor, the pupil (one's eye) detection sensor, and the brainwave detection sensor included in the electronic device.

According to various aspects, the data processing module 105 may incorporate at least one of 3-dimensional coordinate information, slope information of the electronic device, moving direction information in the case where the electronic device moves, movement information, vibration state information, velocity or acceleration information, heat emission state information inside the electronic device, heat emission state information of a display module, color display state information of the display module, luminance sensor information, height information, proximity state information into the context awareness.

According to various aspects, the data processing module 105 may incorporate a correction engine for correcting the least one of the temperature information and the humidity information correction engine based on a combination of one or more ranges designated in a table of one or more sensors detecting the context awareness into the correction value. The table includes mapping information for, for example, the 3-dimensional coordinate information, slope information of the electronic device and moving direction information in the case where the electronic device moves, movement information, vibration state information which are described above.

According to various aspects, the data processing module 105 may incorporate a correction engine for correcting the least one of the temperature information and the humidity information correction engine based on heat emission information of the display module corresponding to a color code regarding one or more colors displayed on the display module. The heat emission information mean amount of heat emitted by the display when a particular color (or set of colors) displayed.

According to various aspects, the data processing module 105 may correct at least one of the temperature information and the humidity information based on at least one of second temperature information and second humidity information and the context awareness.

According to various aspects, the data processing module 105 may receive the second temperature information and the second humidity information, all or a portion of one or more correction engines from one or more other electronic devices connected with the electronic device via a network connection.

According to various aspects, the data processing module 105 may determine the correction value in a database in which mapping data are formed based on two or more correction engines which are used respectively for two or more temperature (humidity) sensors of the electronic device.

Figure 3:
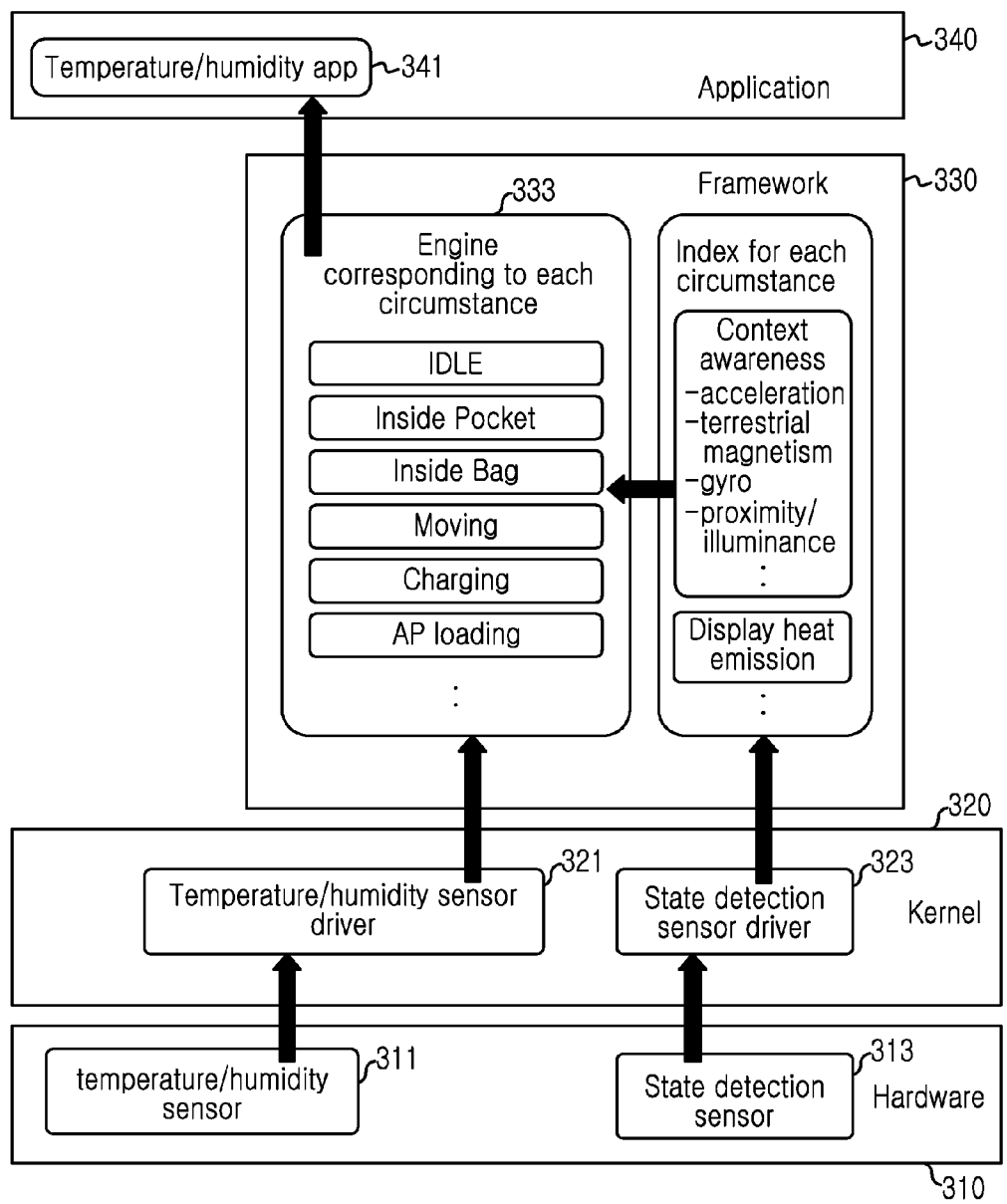
FIG. 3 is a view illustrating an operation of the electronic device 101 in an electronic device according to various aspects.

FIG. 3 is a diagram illustrating an example of a data flow within the electronic device 101, according to various aspects.

The electronic device 101 may obtain internal and/or external temperature/humidity of the electronic device 101 and context awareness of the electronic device 101 via the temperature/humidity sensor 170 and/or the state detection sensor 180. The electronic device 101 may determine a correction engine stored in advance in the electronic device 101 that matches the state of the electronic device 101 via sensing information obtained by one or more sensors. When the electronic device 101 measures temperature/humidity of the inside or the outside of the electronic device 101 using the temperature/humidity sensor 170, an interference may be generated by heat generating from one or more devices forming the inside of the electronic device 101. The electronic device 101 may obtain state information regarding the exterior and/or interior the of the electronic device 101 using the state detection sensor 180 included in the electronic device 101. According to an aspect, the state detection sensor 180 of the electronic device 101 may include at least one of various sensors such as an acceleration sensor, a slope sensor, a gyroscope, a geomagnetic sensor, a GPS, an luminance sensor, a pupil (one's eye) detection sensor, and a brainwave detection sensor, and determine a sensor information of the circumstance of the electronic device 101 corresponding to a predetermined region in a table e.g., of each sensor. The table includes mapping between reference data and the sensor information in order to decide a correction engine. The electronic device 101 may set a correction engine that may correct an error of temperature/humidity obtained by the temperature/humidity sensor 170 of the electronic device 101 in response to determined one or more correction engines.

Here, the correction engine may be a physically configured (e.g., hardware) module that operates to reduce an error between temperature and/or humidity information regarding the interior and/or exterior of the electronic device 101 obtained by the temperature/humidity sensor 170 of the electronic device 101 and actual temperature and/or humidity in response to context awareness of the electronic device 101, or may be a logic (e.g., software) module including an algorithm for processing to reduce an error between temperature and/or humidity information regarding the inside/outside of the electronic device 101 obtained by the temperature/humidity sensor 170 of the electronic device 101 and actual temperature and/or humidity in response to context awareness of the electronic device 101. The electronic device 101 may include a plurality of correction engines corresponding to one or more correction engines configured with reference to sensing information of the state detection sensor 180 and a performance table of the state detection sensor 180, and determine a correction engine of the electronic device 101 to correct temperature/humidity information obtained by the temperature/humidity sensor 170 using the correction engine corresponding to the determined correction engine.

According to some aspects, the electronic device 101 may obtain temperature/humidity information of the interior and/or exterior of the electronic device 101, and context awareness of the electronic device 101 via the temperature/humidity sensor 170 and the state detection sensor included in a hardware region 310. The electronic device 101 may control the temperature/humidity sensor 170 and the state detection sensor 180 via a temperature/humidity sensor driver 321 or a state detection sensor driver 323 of a kernel region 320 in operating the temperature/humidity sensor 170 and the state detection sensor 180. A driver corresponding to each sensor may obtain information measured via each sensor. The electronic device 101 may determine a correction engine 333 that matches state information 331 regarding the inside or the outside of the electronic device 101 obtained by the state detection sensor 180 of the electronic device 101 in a framework region 330. The electronic device 101 may then apply a correction engine corresponding to the determined correction engine to correct temperature/humidity obtained by the temperature/humidity sensor 170 of the electronic device 101. The electronic device 101 may display corrected temperature/humidity information or temperature/humidity information that is being corrected on the display module 150 of the electronic device 101. According to an aspect, the electronic device 101 may display temperature/humidity information on the display module 150 depending on User Interface (UI) configuration of a temperature/humidity application 341 included in an application region 340 in displaying temperature/humidity information on the display module.

Figure 4A:
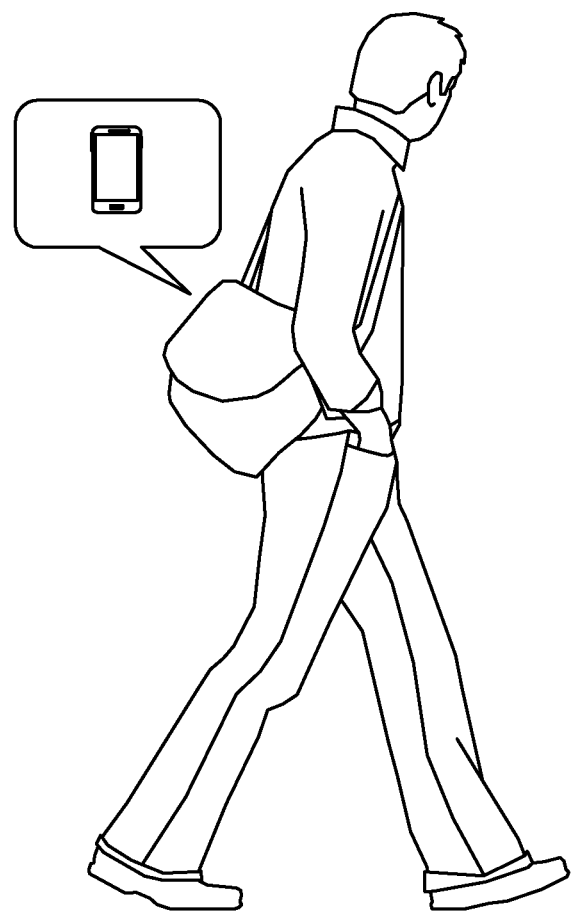
FIG. 4A and FIG. 4B are views illustrating an operation depending on context awareness of the electronic device 101 in an electronic device according to various aspects.
Figure 4B:
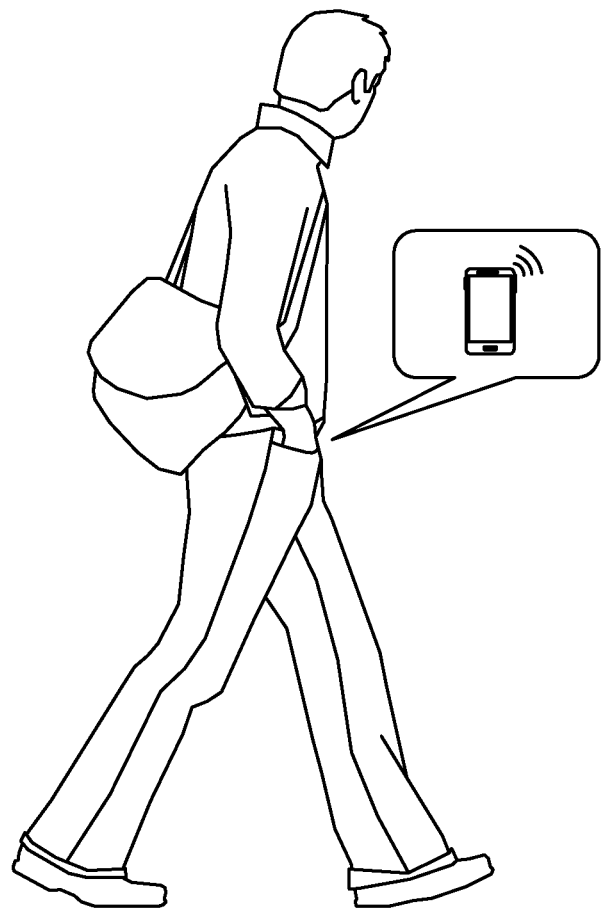

FIGS. 4A and 4B are views illustrating an operation depending on context awareness of the electronic device 101 in an electronic device according to various aspects.

Hereinafter, various aspects of the present disclosure are described with reference to FIG. 4A.

Referring to FIG. 4A, the electronic device 101 may refer to context information (e.g., position information) of one or more electronic devices 101 obtained by the state detection sensor 180 of the electronic device 101 in correcting temperature/humidity information obtained by the temperature/humidity sensor 170. According to an aspect, the electronic device 101 may obtain a state of the electronic device 101 using the state detection sensor 180 while the electronic device 101 is contained in a user's bag (e.g., back pack). For example, a proximity sensor forming the state detection sensor 180 of the electronic device 101 may measure an adjacent object while the electronic device 101 is placed in a user's back pack. In case where one or more objects contained in the user's back pack are not positioned at a designated distance from the proximity sensor of the electronic device 101, the electronic device 101 may obtain location information regarding the interior of the user's back pack in. A luminance sensor forming the state detection sensor 180 of the electronic device 101 may obtain ambient illuminance information of the electronic device 101 while the electronic device 101 is included in the user's back pack. As described above, the electronic device 101 may determine a correction engine of the electronic device 101 based on one or more sensing information (e.g.: context awareness of the electronic device 101) obtained by one or more sensors included in the state detection sensor. Here, the correction engine determined by the electronic device 101 may be one correction engine that matches sensing information among a plurality of correction engines designated with reference to a performance table regarding one or more sensors in the memory (e.g., a database) of the electronic device 101. According to an aspect, in the description of FIG. 4A, the electronic device 101 may determine a correction engine corresponding to 'inside bag' of the correction engine 333 of FIG. 3 with reference to sensing information. The electronic device 101 may correct temperature/humidity information obtained by the temperature/humidity sensor 170 of the electronic device 101 using a designated correction engine corresponding to the determined correction engine 'inside bag'.

Referring to FIG. 4B, the electronic device 101 may refer to context information (e.g., e.g., position information) of one or more electronic devices 101 obtained by the state detection sensor 180 of the electronic device 101 in correcting temperature/humidity information obtained by the temperature/humidity sensor 170. According to an aspect, the electronic device 101 may obtain a state of the electronic device 101 using the state detection sensor 180 while the electronic device 101 is contained in a pocket closely attached to a user (e.g., a trouser pocket). For example, a proximity sensor forming the state detection sensor 180 of the electronic device 101 may detect an adjacent object while the electronic device 101 is placed in a user's pocket. A luminance sensor forming the state detection sensor 180 of the electronic device 101 may obtain ambient luminance information of the electronic device 101 while the electronic device 101 is placed in the user's pocket. As described above, the electronic device 101 may determine a correction engine of the electronic device 101 based on one or more items of sensed information (e.g., context awareness of the electronic device 101) obtained by one or more sensors included in the state detection sensor. Here, the correction engine is selected by the electronic device 101 among a plurality of correction engines designated based on a table regarding one or more sensors in the memory (e.g., a database) of the electronic device 101. According to an aspect, in the description of FIG. 4A, the electronic device 101 may identify a correction engine corresponding to correction engine a state of the electronic device 101 in which the electronic device 101 is inside a user's pocket sensed information. The electronic device 101 may correct temperature/humidity information obtained by the temperature/humidity sensor 170 of the electronic device 101 using a designated correction engine of the identified correction engine.

The electronic device 101 may determine a correction engine based on a correction engine regarding an operation that is being performed by the electronic device 101 together with the above-described context awareness of the electronic device 101 (e.g., position state information such as 'inside bag' or 'inside pocket') in correcting temperature/humidity information obtained by the temperature/humidity sensor 170. According to an aspect, the electronic device 101 may obtain information regarding 'heat emission state' by an operation performed by the electronic device 101 together with a correction engine corresponding to the above-described 'inside pocket'. The electronic device 101 may determine a correction engine corresponding to 'inside packet' and a correction engine that matches information regarding 'heat emission state' based on a database, and correct temperature/humidity information obtained by the temperature/humidity sensor 170 of the electronic device 101 using the determined correction engine.

Hereinafter, various aspects of the present disclosure are described based on FIG. 4B.

Referring to FIG. 4B, the electronic device 101 may refer to context information (e.g., operation information) of one or more electronic devices 101 obtained by the state detection sensor 180 of the electronic device 101 in correcting temperature/humidity information obtained by the temperature/humidity sensor 170. The electronic device 101 may apply a correction engine determined based on context awareness of one or more electronic devices 101 obtained by the state detection sensor 180 of the electronic device 101 to correct temperature/humidity information obtained by the temperature/humidity sensor 170 of the electronic device 101. According to an aspect, the electronic device 101 may be moving, and perform one or more functions while moving. The electronic device 101 may obtain temperature/humidity information of the inside/outside of the electronic device 101 using the temperature/humidity sensor 170 while moving, and obtain state information (e.g., information such as a moving velocity, a moving direction, a movement pattern) of the electronic device 101 using the state detection sensor 180 of the electronic device 101. For example, the acceleration sensor forming the state detection sensor 180 of the electronic device 101 may obtain velocity information with which the electronic device 101 moves. The gyro sensor forming the state detection sensor 180 of the electronic device 101 may obtain direction information in which the electronic device 101 moves. As described above, in the case where sensing information regarding a pattern of 'moving' and a correction engine (e.g., a correction engine 'moving') designated based on the sensing information are included in the database of the electronic device 101, the electronic device 101 may determine the correction engine 'moving' included in the database of the electronic device 101 that matches the sensing information obtained by the state detection sensor 180. The electronic device 101 may correct the temperature/humidity information obtained by the temperature/humidity sensor 170 of the electronic device 101 using a designated correction engine of the determined correction engine 'moving'.

Referring to FIG. 4B, the electronic device 101 may refer to context information (e.g., operation information) of one or more electronic devices 101 obtained by the state detection sensor 180 of the electronic device 101 in correcting temperature/humidity information obtained by the temperature/humidity sensor 170. The electronic device 101 may apply a correction engine determined based on context awareness of one or more electronic devices 101 obtained by the state detection sensor 180 of the electronic device 101 to correct temperature/humidity information obtained by the temperature/humidity sensor 170 of the electronic device 101. According to an aspect, the electronic device 101 may be moving, and perform one or more functions while moving. The electronic device 101 may obtain temperature/humidity information of the inside/outside of the electronic device 101 using the temperature/humidity sensor 170 while moving, and obtain state information (e.g., information such as a moving velocity, a moving direction, a movement pattern) of the electronic device 101 using the state detection sensor 180 of the electronic device 101. For example, the acceleration sensor forming the state detection sensor 180 of the electronic device 101 may obtain velocity information with which the electronic device 101 moves. The gyro sensor forming the state detection sensor 180 of the electronic device 101 may obtain direction information in which the electronic device 101 moves. In addition, the electronic device 101 may obtain sensing information of a case where a user is running while carrying the electronic device 101 via at least one of the gyro sensor, the acceleration sensor, the slope sensor, and the geomagnetic sensor forming the state detection sensor 180, and obtain a repeated pattern (e.g., a movement pattern of the electronic device 101 by a 'running' operation) in the obtained sensing information. In the case where sensing information regarding the pattern of 'running' and a correction engine (e.g., a correction engine 'running') designated based on the sensing information are included in a database of the electronic device 101, the electronic device 101 may determine the correction engine 'running' included in the database of the electronic device 101 that matches sensing information obtained by the state detection sensor 180. The electronic device 101 may correct temperature/humidity information obtained by the temperature/humidity sensor 170 of the electronic device 101 using a designated correction engine of the determined correction engine 'running'.

Figure 5A:
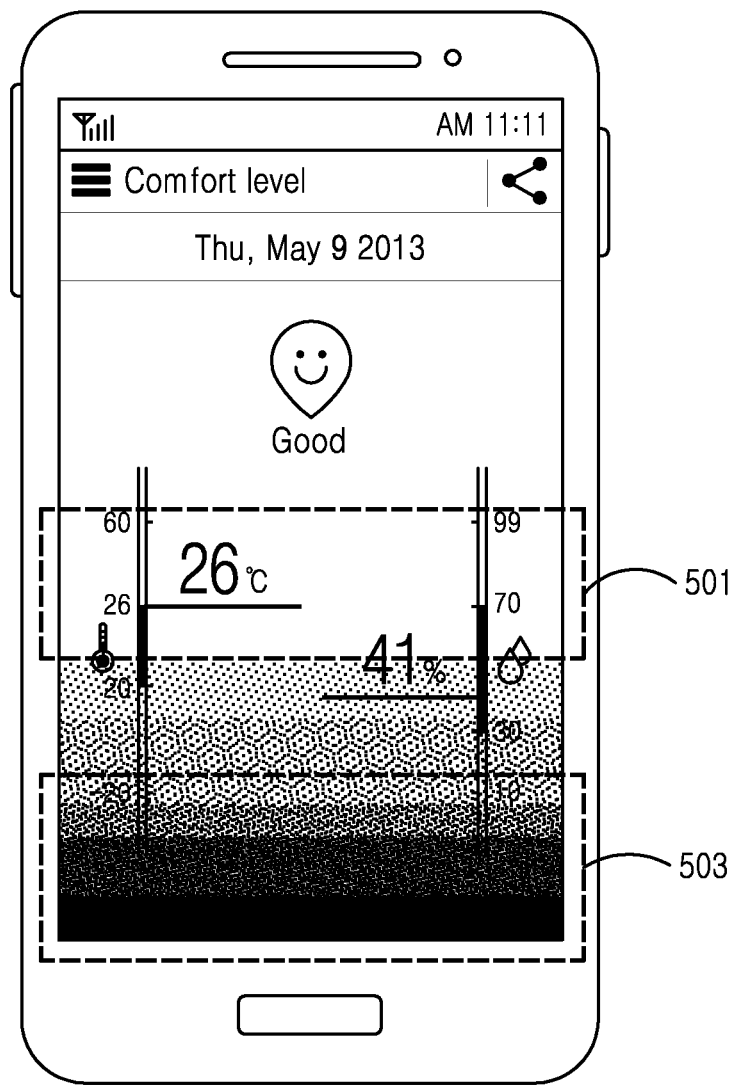
FIG. 5A and FIG. 5B are views illustrating an operation depending on an output of the electronic device 101 in an electronic device according to various aspects.
Figure 5B:

FIGS. 5A and 5B are views illustrating an operation depending on an output of the electronic device 101 in an electronic device according to various aspects.

Referring to FIG. 5A, the electronic device 101 may output (display) screen configuration corresponding to an operation that is being performed by the electronic device 101 via the display module 150 of the electronic device 101. The electronic device 101 may obtain color information used for outputting screen configuration on the display module 150. The electronic device 101 may determine heat emission information that may occur in response to color information used for screen configuration output on the display module 150 in the database. According to an aspect, in the case where the display module 150 of the electronic device 101 is an Active Matrix Organic Light Emitting Diodes (AMOLED), the display module 150 may be a display module that outputs screen configuration using light emitting devices of red, green, and blue colors. The electronic device 101 may apply power to light emitting devices of red, green, and blue colors in a designated method to represent various colors. Since the electronic device 101 applies power to all of light emitting devices of red, green, and blue colors in case of white series color 501, heat emission may be large compared to black series color 503. The electronic device 101 may incorporate heat emission information corresponding to one or more colors represented by application of power to light emitting devices of red, green, and blue colors into the database. The electronic device 101 may determine a designated correction engine with reference to color information of screen configuration that is being output on the display module 150 and heat emission information corresponding to the color information. The color information may be the average of the RGB values of a set of pixels. Here, average of a set of pixels may be used. Also, the metric may be calculated for all pixels in the display or a subset of the display's pixels. The electronic device 101 may apply the designated correction engine to correct temperature/humidity information obtained by the temperature/humidity sensor 170.

According to an aspect, the electronic device 101 may incorporate one or more designated programs among programs included in the electronic device, or index information regarding one or more screen configurations among screen configurations corresponding to an operation performed by a program into the database, and incorporate a correction engine designated by one or more indexes into the database. In instances in which a designated program operates or designated screen configuration is output, the electronic device 101 may apply a corresponding correction engine and correct temperature/humidity information obtained via the temperature/humidity sensor 170 of the electronic device 101. Though the electronic device 101 may incorporate the above-described index information into the database of the electronic device, but it is not limited thereto and the electronic device 101 may generate the index information with reference to sensing information obtained by the temperature/humidity sensor 170 and/or the state detection sensor 180 of the electronic device 101, or obtain the index information from other electronic devices connected via network communication.

Referring to FIG. 5B, the electronic device 101 may incorporate a color table regarding one or more colors that may be represented via the display module 150 of the electronic device 101 into the database. In case of displaying screen configuration regarding one or more operation states that are operating in the electronic device 101 on the display module 150, the electronic device 101 may obtain color information used for screen configuration. The screen configuration is, for example, a configuration of state of the displayed image or a configuration of icons or a configuration of color of the screen or a configuration of brightness of the screen. The electronic device 101 may obtain a color information 501 based on a percentage of a used color in which the used color forms above threshold value in screen configuration. The electronic device 101 may determine a corresponding correction engine or a corresponding correction engine with reference to a used color code and heat emission data of the ratio information 501 of the color code.

Figure 6:
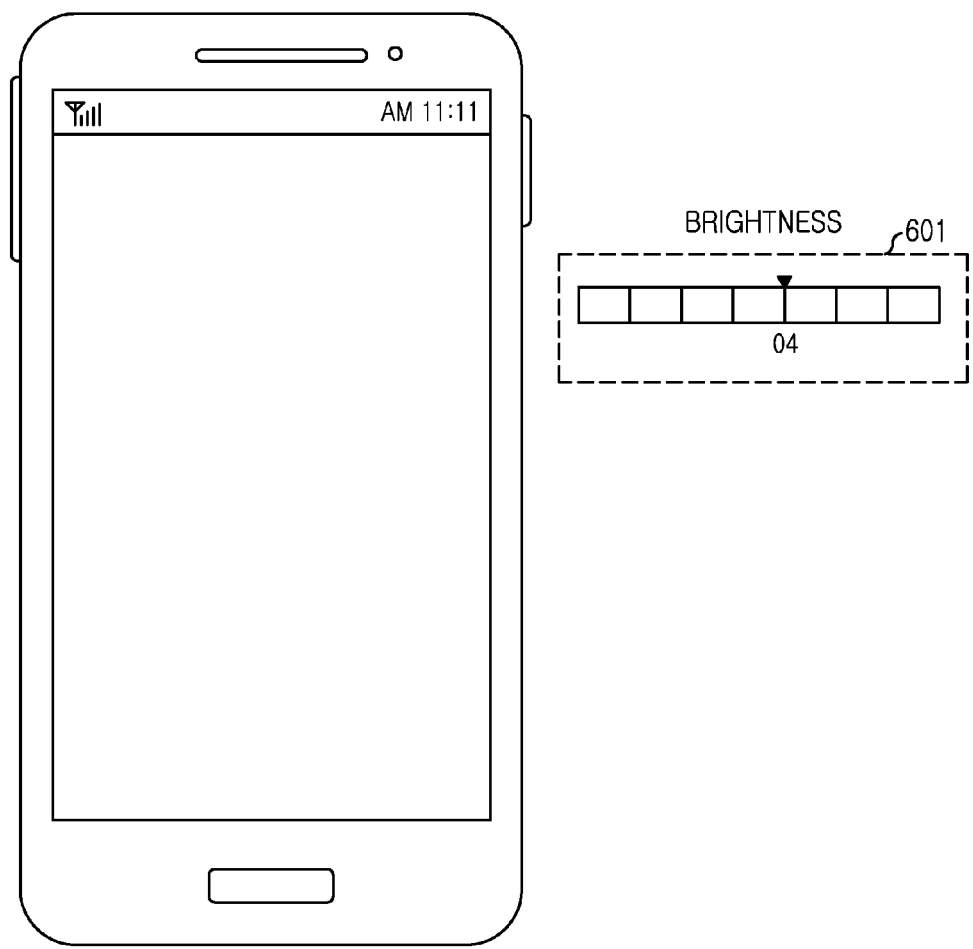
FIG. 6 is a view illustrating an operation depending on a display state in an electronic device according to various aspects.

FIG. 6 is a view illustrating an operation depending on a display state in an electronic device according to various aspects.

The electronic device 101 may determine a corresponding correction engine depending on brightness of the display module 150, and apply the determined correction engine to correct temperature/humidity information obtained via the temperature/humidity sensor 170 of the electronic device 101. Referring to FIG. 6, the electronic device 101 may provide a menu 601 (e.g., a menu for controlling brightness of the display module 150) for controlling one or more light emitting devices that control brightness of the display module 150 in outputting screen configuration corresponding to an operation performed by the electronic device 101 on the display module. The electronic device 101 may divide brightness of the display module 150 into one or more levels (or steps) via a menu for controlling the brightness of the display module 150 and control the same. The electronic device 101 may incorporate a designated correction engine corresponding to divided each brightness level into the database, and determine a correction engine corresponding to a set brightness level (e.g., 'brightness level 04' set in the menu 601 for controlling brightness of the display module 150).

According to an aspect, the electronic device 101 may detect that the brightness of the display module 150 of the electronic device 101 has changed during an operation of correcting temperature/humidity information obtained by the temperature/humidity sensor 170 of the electronic device 101 with reference to brightness information (e.g., a brightness level) of the display module 150 of the electronic device 101. The electronic device 101 may determine a relevant correction engine with reference to changed brightness information of the display module 150. The electronic device 101 may combine a first correction engine determined with reference to brightness information of the display module 150 before temperature/humidity information correction, and a second correction engine determined with reference to brightness information of the display module 150 changed during correction in a designated method to generate a third correction engine, correct temperature/humidity information using the third correction engine, or apply the second correction engine to correct temperature/humidity information.

Figure 7:
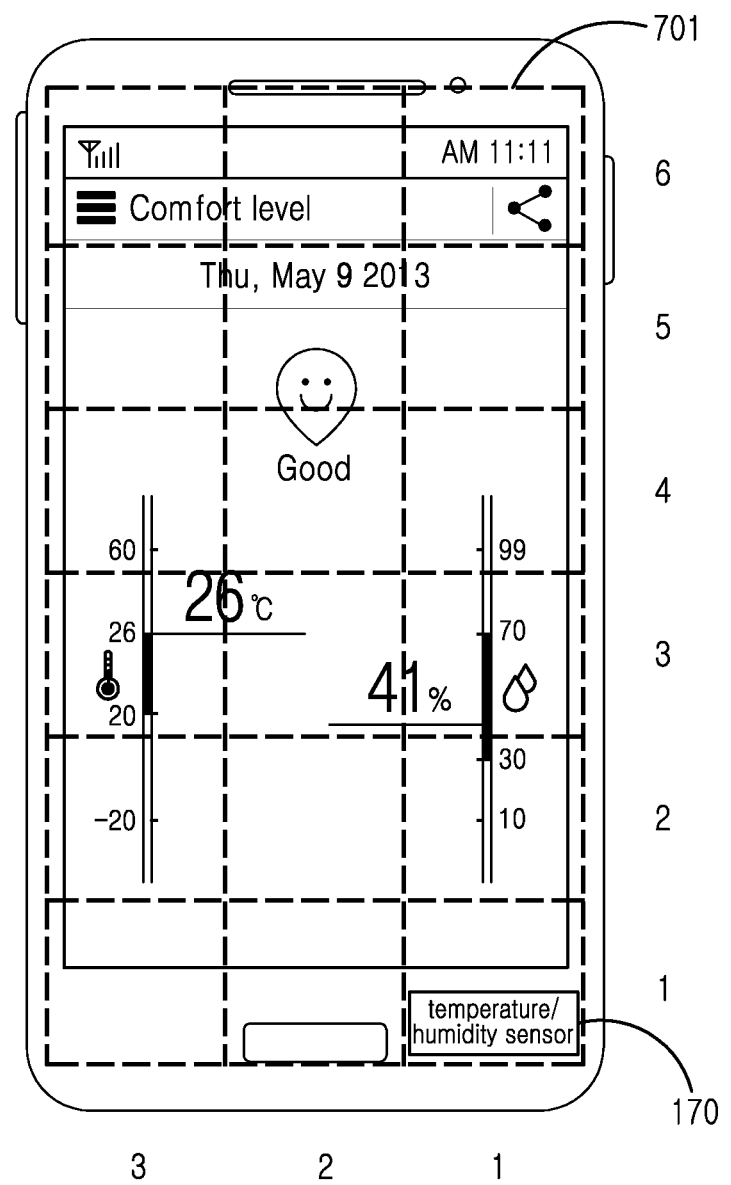
FIG. 7 is a view illustrating an operation depending on a position of a temperature/humidity sensor 170 in an electronic device according to various aspects.

FIG. 7 is a view illustrating an operation depending on a position of a temperature/humidity sensor 170 in an electronic device according to various aspects.

In case of obtaining an inner temperature of the electronic device 101 using the temperature/humidity sensor 170 in a circumstance of one or more heat emitting bodies (e.g., devices), the inner structure of the electronic device 101, or the position of the temperature/humidity sensor 170, the electronic device 101 may obtain temperature/humidity information of different values even under the same temperature. Referring to FIG. 7, a coordinate 701 displayed on the electronic device 101 may be a vector coordinate that discriminates the inner region of the electronic device 101. Though the temperature/humidity sensor 170 may directly measure temperature/humidity, it may obtain temperature of devices positioned in an inner predetermined region of the electronic device 101 using a wire (e.g., a conduction wire between substrates or modules) inside the electronic device 101, and receive temperature information and/or humidity information obtained by one or more temperature sensors and/or humidity sensors that measure temperature of a device positioned in an inner predetermined region of the electronic device 101.

Referring to FIG. 7, according to an aspect, the temperature/humidity sensor 170 may be positioned in a designated region of 1*1 (width*length) inside the electronic device 101. In case of obtaining temperature of a first device that emits heat at 49° C. connected via a conduction wire positioned in a designated region of 3*6 inside the electronic device 101 and temperature of a second device that emits heat at 49° C. connected via a conduction wire positioned in a designated region of 2*2 inside the electronic device 101, an interference may occur due to an inner state of the electronic device 101 when the electronic device 101 obtains the temperature of the first device. Therefore, the temperature/humidity sensor 170 may obtain the temperatures of the first device and the second device that are emitting heat at the same temperature inside the electronic device 101 as temperatures of different values. The electronic device 101 may incorporate a correction engine that may correct temperature/humidity obtained by the temperature/humidity sensor 170 of the electronic device 101 with reference to a condition under which an interference may occur depending on an inner state of the electronic device 101 as described above into the database. The electronic device 101 may apply a correction engine corresponding to a designated position to temperature/humidity obtained at the designated position inside the electronic device 101 to correct the same.

Figure 8A:
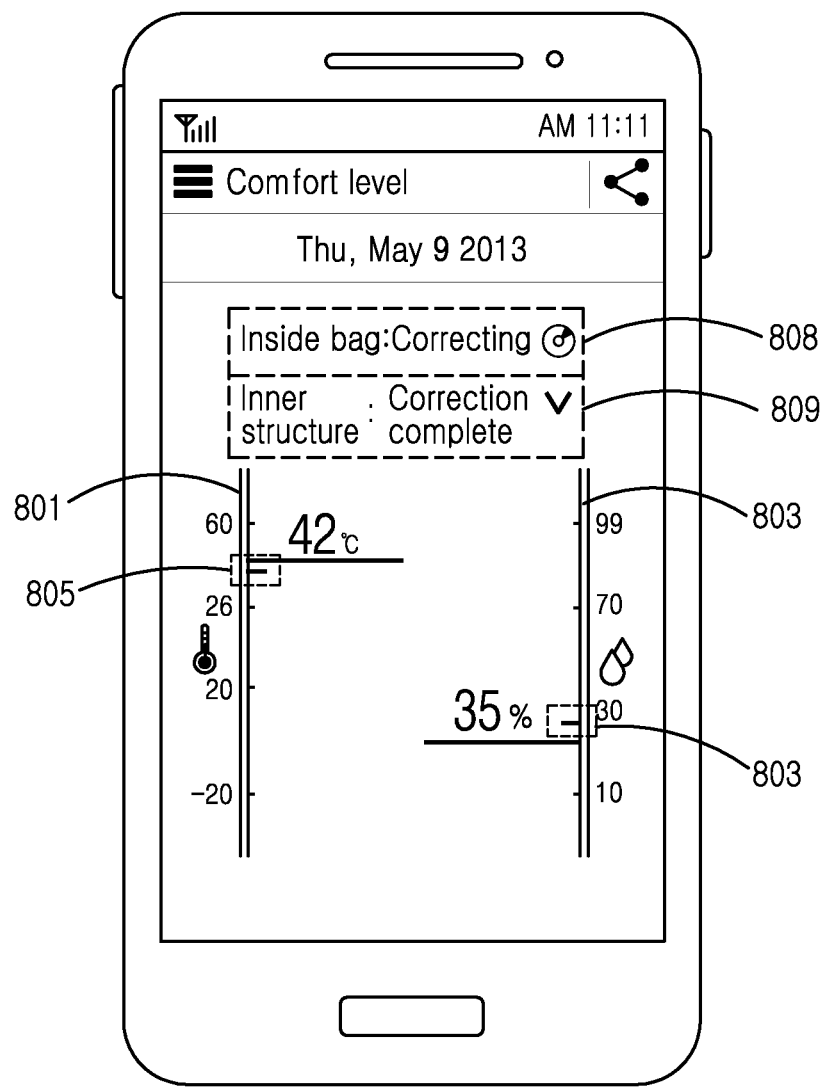
FIG. 8A and FIG. 8B are views illustrating an operation of displaying temperature/humidity information in an electronic device according to various aspects.
Figure 8B:
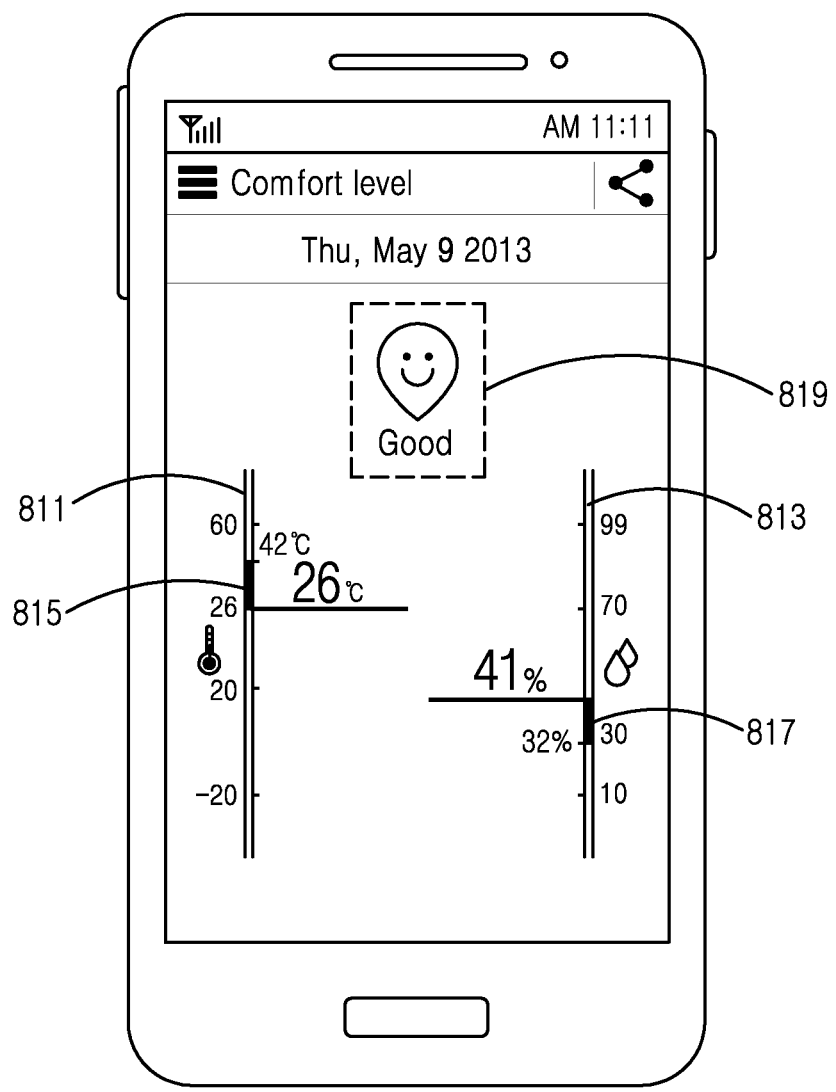

FIGS. 8A and 8B are views illustrating an operation of displaying temperature/humidity information in an electronic device according to various aspects.

The electronic device 101 may output temperature/humidity information obtained by the temperature/humidity sensor 170 via one or more output units such as the display module 150 or the speaker module (not shown). In case of displaying temperature/humidity information using the display module 150, the electronic device 101 may display one or more information related to correction of temperature/humidity information such as temperature/humidity information obtained by the temperature/humidity sensor 170, temperature/humidity information that is being corrected (e.g., a correction process may be displayed) by one or more correction engines, and a temperature/humidity information difference before/after correction.

Hereinafter, various aspects of the present disclosure are described with reference to FIG. 8.

Referring to FIG. 8A, the electronic device 101 may display temperature information (e.g., temperature information 801) and/or humidity information (e.g., humidity information 803) obtained by the temperature/humidity sensor 170 on the display module 150. The electronic device 101 may display one or more correction engines (e.g., inside bag and an inner structure) determined with reference to context awareness of the electronic device 101 in order to correct a temperature/humidity information error that that is the result of the current context of the electronic device 101. For example, in case of applying a correction engine 'inside bag' determined with reference to obtained context awareness of the electronic device 101 and performing correction, the electronic device 101 may display an indication of the correction such as 'inside bag: correcting 808' and/or a mark corresponding to correcting. In case of applying a correction engine 'inner condition' determined with reference to obtained context awareness of the electronic device 101 and completing correction, the electronic device 101 may display an indication that the correction is complete, such as 'inner structure: correction complete 809'. The electronic device may display an indication of temperature 805 and an indication of the humidity 807.

Referring to FIG. 8B, the electronic device 101 may display temperature/humidity information before correction obtained by the temperature/humidity sensor 170 of the electronic device 101 and/or temperature/humidity information after correction. According to an aspect, the electronic device 101 may display temperature information (e.g., 42° C.) and humidity information (e.g., 32%) before correction, obtained by the temperature/humidity sensor 170 at temperature information 811 and humidity information 813 displayed on the display module 150. The electronic device 101 may display corrected temperature information (e.g., 26° C.) with application of one or more correction engines determined with reference to context awareness of the electronic device 101 and a difference 815 between temperature information (e.g., 42° C.) before correction and temperature information (e.g., 26° C.) after correction, and display humidity information (e.g., 41%) and a difference 817 between humidity information (32%) before correction and humidity information (41%) after correction. In the case where a user selects the difference 815 in the temperature information or the difference 817 in the humidity information displayed on the display module 150, the electronic device 101 may additionally display information regarding applied one or more correction engines and/or error information.

The electronic device 101 may receive a correction engine or temperature/humidity information of an area where the electronic device 101 is positioned from one or more other electronic devices connected via network communication. The electronic device 101 may display state information 819 corresponding to a numerical value obtained by comparing temperature information and/or humidity information corrected with application of a correction engine with temperature information and/or humidity information received via the network communication.

Figure 9:
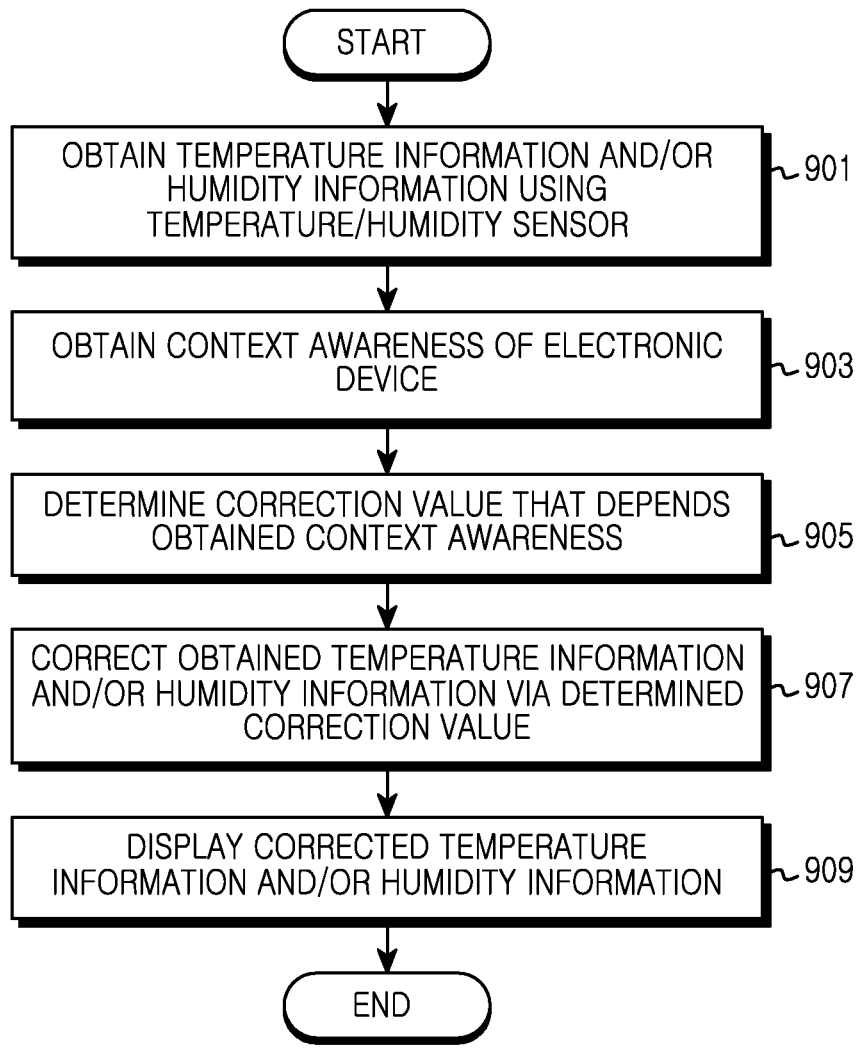
FIG. 9 is a flowchart illustrating an operation of correcting temperature/humidity information obtained in an electronic device according to various aspects.

FIG. 9 is a flowchart illustrating an operation of correcting temperature/humidity information obtained in an electronic device according to various aspects.

In operation 901, the electronic device 101 may obtain a temperature and/or a humidity reading from the temperature/humidity sensor 170.

In operation 903, the electronic device 101 may obtain context awareness of the electronic device using the state detection sensor 180. Obtaining the context awareness of the electronic device may include obtaining an indication of the state of the electronic device. In some implementations, for example, the indication of the state may be obtained using any suitable sensor that is part of the electronic device 101, such as the state detection sensor. As noted above, the state detection sensor 180 may be used to detect any suitable indication of the state of the electronic device 101, such as heat emission state information inside the electronic device, heat emission state information of the display module 150, color display state information of the display module 150, luminance sensor information, vibration state information, acceleration information, slope information, height information, and proximity state information.

In operation 905, the electronic device 101 may determine a correction value that may correct temperature/humidity information obtained by the temperature/humidity sensor 170 of the electronic device 101 with reference to one or more state information.

Here, the above-described correction value may include a correction engine stored in the database that matches circumstance information determined by combination of one or more information among state information obtained by the electronic device 101, or a correction engine that corrects temperature/humidity information depending on the correction engine. According to an aspect, the electronic device 101 may determine a correction engine that matches information generated by combination of one or more information among obtained state information. Here, the correction engine may be determined corresponding to a combination of values of a designated range among values that may be measured by sensors included in the state detection sensor 180 of the electronic device 101.

According to the above various aspects, though it has been described that one or more correction engines may be provided in response to a correction engine, it is not limited thereto, and one correction engine that operates values included in the determined correction engine and corrects temperature/humidity information may be configured. Also, a plurality of correction engines may be configured as a database that may interact with each other. According to an aspect, the electronic device 101 may omit an operation that determines a correction engine via state information obtained by the state detection sensor 180, and therefore, determine a correction engine corresponding to at least one of state information obtained by the state detection sensor 180 of the electronic device 101.

In operation 907, the electronic device 101 may generate an adjusted reading based on the correction value. Generating the adjusted reading may include adding or subtracting the correction value from the reading obtained at operation 901.

In operation 909, the electronic device may perform an action based on the adjusted reading. In some implementations, generating the adjusted reading may include displaying the adjusted reading. Additionally, or alternatively, generating the adjusted reading may include.

Figure 10:
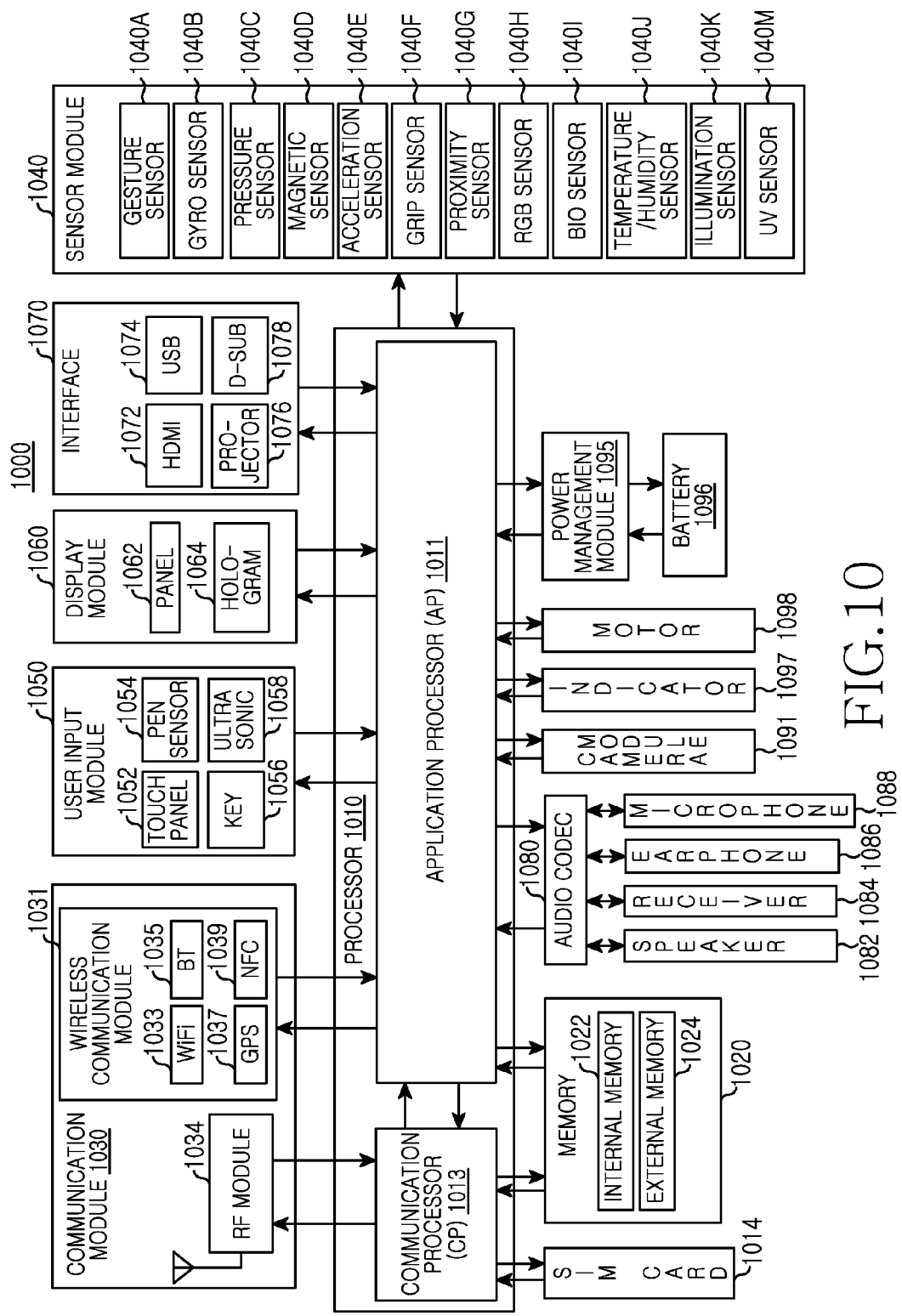
FIG. 10 is a block diagram illustrating a hardware according to various aspects.

FIG. 10 is a block diagram illustrating a hardware according to various aspects.

The hardware 1000 may configure all or a portion of the electronic device 101 illustrated in FIG. 1. Referring to FIG. 10, the hardware 1000 may include one or more processors 1010, a Subscriber Identification Module (SIM) card 1014, a memory 1020, a communication module 1030, a sensor module 1040, a user input module 1050, a display module 1060, an interface 1070, an audio codec 1080, a camera module 1091, a power management module 1095, a battery 1096, an indicator 1097, or a motor 1098.

The processor 1010 (e.g., the processor 120) may include one or more application processors (APs) 1011 or one or more communication processors (CPs) 1013. The processor 1010 may be, for example, the processor 120 illustrated in FIG. 1. Though the AP 1011 and the CP 1013 are included inside the processor 1010 in FIG. 10, the AP 1011 and the CP 1013 may be included in different IC packages, respectively. According to an aspect, the AP 1011 and the CP 1013 may be included in one IC package.

The AP 1011 may drive an Operating System (OS) or an application to control a plurality of hardwares or software elements connected to the AP 1011, and perform various data processings including multimedia data and an operation. The AP 1011 may be implemented, for example, a System on Chip (SoC). According to an aspect, the processor 1010 may further include a Graphic Processing Unit (GPU) (not shown).

The CP 1013 may perform a function of managing a data link and converting a communication protocol in communication between other electronic devices connected with the electronic device (e.g., the electronic device 101) including the hardware 1000. The CP 1013 may be implemented as an SoC, for example. According to an aspect, the CP 1013 may perform at least a portion of a multimedia control function. The CP 1013 may perform, for example, discrimination and authentication of a terminal inside a communication network using a Subscriber Identification Module (SIM) (e.g., a SIM card 1014). Also, the CP 1013 may provide services such as voice communication, video communication, a text message, or packet data, etc. to a user.

Also, the CP 1013 may control data transmission/reception of the communication module 1030. Though elements such as the CP 1013, the power management module 1095, or the memory 1020, etc. are illustrated as elements separated from the AP 1011 in FIG. 10, according to an aspect, the AP 1011 may be implemented to include at least a portion (e.g., the CP 1013) of the above-described elements.

According to an aspect, the AP 1011 or the CP 1013 may load an instruction or data received from at least one of a non-volatile memory or other elements connected thereto to a volatile memory and process the same. Also, the AP 1011 or the CP 1013 may store data received from at least one of other elements or generated by at least one of other elements in a non-volatile memory.

The SIM card 1014 may be a card that implements a subscriber identify module and may be inserted into a slot formed in a specific position of an electronic device. The SIM card 1014 may include unique identify information (e.g., Integrated Circuit Card Identifier (ICCID)) or subscriber information (e.g., International Mobile Subscriber Identity (IMSI)).

The memory 1020 may include a built-in memory 1022 or an external memory 1024. The memory 1020 may be, for example, the memory 130 illustrated in FIG. 1. The built-in memory 1022 may include at least one of a volatile memory (for example: dynamic RAM (DRAM), static RAM (SRAM), synchronous dynamic RAM (SDRAM), etc.) and a non-volatile memory (for example, one time programmable ROM (OTPROM), programmable ROM (PROM), erasable and programmable ROM (EPROM), electrically erasable and programmable ROM (EEPROM), mask ROM, flash ROM, NAND flash memory, NOR flash memory, etc.). According to an aspect, the built-in memory 1022 may have a form of a Solid State Drive (SSD). The external memory 1024 may further include a flash drive, for example, compact flash (CF), secure digital (SD), micro secure digital (Micro-SD), mini secure digital (Mini-SD), extreme digital (xD), or a memory stick, etc.

The communication module 1030 may include a wireless communication module 1031 or an RF module 1034. The communication module 1030 may be, for example, the communication module 170 illustrated in FIG. 1. The wireless communication module 1031 may include, for example, Wi-Fi 1033, bluetooth (BT) 1035, a GPS 1037, or near field communication (NFC) 1039. For example, the wireless communication module 1031 may provide a wireless communication function using a radio frequency. Additionally, or alternatively, the wireless communication module 1031 may include a network interface (e.g., a LAN card) or a modem, etc. for connecting the hardware 1000 with a network (e.g., the Internet, a Local Area Network (LAN), a Wide Area Network (WAN), a telecommunication network, a cellular network, a satellite network or a plain old telephone service (POTS), etc.).

The RF module 1034 may be responsible for transmission/reception of data, for example, transmission/reception of an RF signal or a called electronic signal. The RF module 1034 may include, though not shown, a transceiver, a power amp module (PAM), a frequency filter or a low noise amplifier (LNA), etc., for example. Also, the RF module 1034 may further include a part for transmitting/receiving a radio wave in a free space in wireless communication, for example, a conductor or a conducting wire, etc.

The sensor module 1040 may include, for example, at least one of a gesture sensor 1040A, a gyro sensor 1040B, an atmospheric pressure sensor 1040C, a magnetic sensor 1040D, an acceleration sensor 1040E, a grip sensor 1040F, a proximity sensor 1040G, an RGB (red, green, blue) sensor 1040H, a living body sensor 1040I, a temperature/humidity sensor 1040J, an luminance sensor 1040K, or an ultra violet (UV) sensor 1040M. The sensor module 1040 may measure a physical quantity or detect an operation state of the electronic device to convert the measured or detected information to an electric signal. Additionally/alternatively, the sensor module 1040 may include, for example, an E-nose sensor (not shown), an electromyography (EMG) sensor (not shown), an electroencephalogram (EEG sensor) (not shown), an electrocardiogram sensor (ECG sensor) (not shown), or a fingerprint sensor, etc. The sensor module 1040 may further include a control circuit for controlling one or more sensors belonging thereto.

The user input module 1050 may include a touch panel 1052, a (digital) pen sensor 1054, a key 1056, or an ultrasonic input unit 1058. The user input module 1050 may be, for example, the I/O interface 140 illustrated in FIG. 1. The touch panel 1052 may recognize a touch input using at least one of capacitive, resistive, infrared or ultrasonic methods. Also, the touch panel 1052 may further include a controller (not shown). The capacitive touch panel may perform proximity recognition as well as direct touch. The touch panel 1052 may further include a tactile layer. In this case, the touch panel 1052 may provide a tactile reaction to a user.

The (digital) pen sensor 1054 may be implemented using a method same as or similar to a method of receiving a user's touch input, or using a separate sheet for recognition. For the key 1056, a keypad or a touch key may be used for example. The ultrasonic input unit 1058 is a device allowing a terminal to detect a sound wave using a microphone (e.g., a microphone 1088) to determine data via a pen that generates an ultrasonic signal, and enables wireless recognition. According to an aspect, the hardware 1000 may receive a user input from an external device (e.g., a network, a computer or a server) connected thereto using the communication module 1030.

The display module 1060 may include a panel 1062 or a hologram 1064. The display module 1060 may be, for example, the display module 150 illustrated in FIG. 1. The panel 1062 may be, for example, a Liquid Crystal Display (LCD) or an Active Matrix Organic Light-Emitting Diode (AMOLED), etc. The panel 1062 may be, for example, implemented such that it is flexible, transparent, or wearable. The panel 1062 may be configured as one module together with the touch panel 1052. The hologram 1064 may show a 3-dimensional image in the air using interference of light. According to an aspect, the display module 1060 may further include a control circuit for controlling the panel 1062 or the hologram 1064.

The interface 1010 may include, for example, a High-Definition Multimedia Interface (HDMI) 1012, a Universal Serial Bus (USB) 1014, a projector 1016, or D-subminiature (D-sub) 1018. Additionally or alternatively, the interface 1010 may include, for example, secure digital (SD)/multimedia card (MMC) (not shown) or infrared data association (IrDA) (not shown).

The audio codec 1080 may convert voice and an electric signal in dual directions. The audio codec 1080 may convert voice information input or output via a speaker 1082, a receiver 1084, an earphone 1086, or a microphone 1088, etc., for example.

The camera module 1091 is a device for shooting an image and a moving picture. According to an aspect, the camera module 1091 may include one or more image sensors (e.g., a front lens or a rear lens), an image signal processor (ISP) (not shown), or a flash LED (not shown).

The power management module 1095 may manage power of the hardware 1000. Though not shown, the power management module 1095 may include, for example, a power management integrated circuit (PMIC), a charger integrated circuit (IC), or a battery fuel gauge.

The PMIC may be mounted inside an integrated circuit or an SoC semiconductor, for example. A charging method may be divided into a wired method and a wireless method. The charging IC may charge a battery, and prevent introduction of an overvoltage or an overcurrent. According to an aspect, the charging IC may include a charging IC for at least one of the wired charging method and the wireless charging method. For the wireless charging method, there are a magnetic resonance method, a magnetic induction method, or an electromagnetic wave method, etc., for example. An additional circuit for wireless charging, for example, a circuit such as a coil loop, a resonance circuit, a rectifier, etc., may be added.

The battery gauge may measure, for example, a remnant of the battery 1096, a voltage, current, or temperature during charging. The battery 1096 may generate electricity to supply power, and may be, for example, a rechargeable battery.

The indicator 1097 may display a specific state of the hardware 1000 or a portion thereof (e.g., the AP 1011), for example, a booting state, a message state, or a charging state, etc. The motor 1098 may convert an electric signal to mechanical vibration. The MCU 1099 may control the sensor module 1040.

Though not shown, the hardware 1000 may include a processing unit (e.g., a GPU) for supporting a mobile TV. The processing unit for supporting the mobile TV may process, for example, media data conforming to a standard such as Digital Multimedia Broadcasting (DMB), Digital Video Broadcasting (DVB), or a media flow, etc. Each of the above-described elements of the hardware according to the present disclosure may be configured using one or more components, and a name of a relevant element may change depending on a kind of an electronic device. The hardware according to the present disclosure may include at least one of the above-described elements, and omit a portion of the elements or further include an additional another element.

Also, a portion of the elements of the hardware according to the present disclosure may combine to form one entity and equally perform the function of the relevant elements before the combination.

According to various aspects, the present disclosure may obtain information regarding an interference of the electronic device that may occur in measuring outside temperature/humidity of the electronic device, and apply a scenario corresponding to context information of the electronic device to correct temperature/humidity information measured by the electronic device so that the measured temperature may come close to actual temperature.

Methods according to the aspects described in claims and/or specification of the present disclosure may be implemented in the form of a hardware, a software, or a combination of the hardware and the software.

In case of implementation using a software, a computer-readable storage medium storing one or more programs (software modules) may be provided. One or more programs stored in the computer-readable storage medium is configured for execution by one or more processors inside the electronic device. One or more programs include instructions allowing the electronic device to execute methods according to the aspects described in claims and/or specification of the present disclosure.

This program (a software module, a software) may be stored in a random access memory, a non-volatile memory including a flash memory, Read Only Memory (ROM), an Electrically Erasable Programmable Read Only Memory (EEPROM), a magnetic disc storage device, a Compact Disc ROM (CD-ROM), Digital Versatile Discs (DVDs), or other types of optical storage devices, and a magnetic cassette. Alternatively, this program may be stored in a memory configured using all or a portion of these. Also, a plurality of respective constituent memories may be provided.

This program may be stored in an attachable storage device that may access the electronic device via a communication network such as the Internet, an Intranet, a Local Area Network (LAN), a Wide LAN (WLAN), or a Storage Area Network (SAN), or a communication network configured using a combination of these. This storage device may access the electronic device via an external port. Also, a separate storage device on a communication network may access a portable electronic device.

In performing various aspects of the present disclosure, the electronic device 100 may perform the aspects via a program of the memory 130, and directly control the aspects by a processor (e.g., the processor 120). Also, the electronic device 100 may perform the aspects via a control module (e.g., the data processing module 105) connected to the processor.

According to various aspects, the processor 120 may control a hardware correction engine that operates to correct at least one of the temperature information and the humidity information obtained by the temperature/humidity sensor of the electronic device with reference to the state information, or a software correction engine including an algorithm that processes to correct at least one of the temperature information and the humidity information obtained by the temperature/humidity sensor of the electronic device with reference to the state information. A terminology "module" used for the present disclosure may mean, for example, a unit including a combination of one or more of a hardware, a software, or a firmware. A "module" may be interchangeably used with a terminology such as a unit, a logic, a logical block, a component, or a circuit, for example. A "module" may be a minimum unit performing one or more functions or a portion thereof. A "module" may be implemented mechanically or electronically. For example, a "module" according to the present disclosure may include at least one of an application-specific integrated circuit (ASIC) chip performing certain operations, field-programmable gate arrays (FPGAs), or a programmable-logic device.

According to various aspects, at least a portion of a device (e.g., modules or functions thereof) or a method according to the present disclosure may be implemented using an instruction stored in a computer-readable storage media in the form of a programming module, for example. The instruction, when executed by one or more processors (e.g., the processor 1011), may allow the one or more processors to perform a function corresponding to the instruction. A computer-readable storage medium may be, for example, the memory 1020. At least a portion of the programming module may be implemented (e.g., executed) by the processor 1011, for example. At least a portion of the programming module may include, for example, a module, an application, a routine, sets of instructions and/or a process, etc. for performing one or more functions.

FIGS. 1-13 are provided as an example only. At least some of the steps discussed with respect to these figures can be performed concurrently, performed in a different order, and/or altogether omitted. It will be understood that the provision of the examples described herein, as well as clauses phrased as "such as," e.g.", "including", "in some aspects," "in some implementations," and the like should not be interpreted as limiting the claimed subject matter to the specific examples.

The above-described aspects of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

Although the disclosure has been shown and described with reference to certain exemplary aspects thereof, it will be understood by those skilled in the art that various changes in form and details may be made therein without departing from the spirit and scope of the disclosure as defined by the appended claims and their equivalents. Therefore, the scope of the present disclosure should not be limited to the above-described aspects but should be determined by not only the appended claims but also the equivalents thereof.

What is claimed is:

1. A method for operating an electronic device, the method comprising:
   obtaining a first information from a first hardware unit, the first hardware unit including at least one of a temperature sensor and a humidity sensor;
   detecting a state of the electronic device using a second hardware unit including a plurality of sensors of the electronic device;
   adjusting the first information based on the state of the electronic device to generate an adjusted information; and
   performing, by the electronic device, an action based on the adjusted information,
   wherein adjusting the first information comprise:
   obtaining information from at least one sensor among the plurality of sensors;
   selecting a correction engine corresponding to the obtained information using a table; and
   generating the adjusted information using the correction engine.

2. The method of claim 1, wherein performing the action based on the adjusted information includes displaying the adjusted information.

3. The method of claim 1, wherein the state of the electronic device is detected using a second hardware unit that, the second hardware unit including at least one of:
   (i) an acceleration sensor,
   (ii) a tilt sensor,
   (iii) a gyroscope,
   (iv) a geomagnetic sensor,
   (v) a Global Positioning System (GPS),
   (vi) an luminance sensor, a proximity sensor,
   (vii) a pupil detection sensor, and a
   (viii) brainwave detection sensor.

4. The method of claim 1, wherein detecting the state of the electronic device includes obtaining an indication of one or more of:
   (i) a 3-dimensional coordinate of a current location of the electronic device,
   (ii) a tilt of the electronic device,
   (iii) a vibration state of the electronic device,
   (iv) a velocity or acceleration of the electronic device,
   (v) a heat emission of the electronic device,
   (vi) heat emission of a display module of the electronic device,
   (vii) a color displayed by one or more pixels of the display module,
   (viii) ambient luminance,
   (ix) a direction of movement of the electronic device, and
   (x) whether any objects are detectable by a proximity sensor of the electronic device.

5. The method of claim 1, wherein each information's corresponding range is identified using a data structure stored in a memory of the electronic device that is associated the information's respective sensor.

6. The method of claim 1, wherein:
   detecting the state of the electronic device includes identifying a color that is displayed by one or more pixels of a display unit of the electronic device; and
   adjusting the first information includes generating the adjusted information based on the first information and the color that is displayed by the one or more pixels.

7. The method of claim 1, further comprising:
   receiving a second information obtained from a third hardware unit; and
   generating the adjusted information based on the first information, the second information, and a distance between the another device and the electronic device,
   wherein the third hardware unit is part of another device connected to the electronic device via a communications network.

8. The method of claim 1, wherein:
   detecting the state of the electronic device includes detecting a brightness level of a display unit of the electronic device; and
   adjusting the first information includes generating the adjusted information based on the first information and the brightness level of the display unit.

9. The method of claim 8, wherein:
   the adjusted information is set to a first value when the brightness level is below a threshold; and
   the adjusted information is set to a second value when the brightness level is above the threshold.

10. An electronic device comprising:
    a first hardware unit including at least one of a temperature sensor and a humidity sensor;
    a second hardware unit including a plurality of sensors of the electronic device; and
    a processing circuitry configured to:
    obtain a first information from the first hardware unit;
    detect a state of the electronic device using the second hardware unit;
    adjust the first information based on the state of the electronic device to generate an adjusted information; and
    perform, by the electronic device, an action based on the adjusted information,
    wherein in order to adjust the first information, the processing circuitry is configured to:
    obtain information from at least one hardware unit among a plurality of hardware units;
    select a correction engine corresponding to the obtained information using a table; and
    generate the adjusted information using the correction engine.

11. The electronic device of claim 10, wherein performing the action based on the adjusted information includes displaying the adjusted information.

12. The electronic device of claim 10, wherein the state of the electronic device is detected using the second hardware unit, the second hardware unit including at least one of:
    (i) an acceleration sensor,
    (ii) a tilt sensor,
    (iii) a gyroscope,
    (iv) a geomagnetic sensor,
    (v) a Global Positioning System (GPS),
    (vi) an luminance sensor, a proximity sensor,
    (vii) a pupil detection sensor, and a
    (viii) brainwave detection sensor.

13. The electronic device of claim 10, wherein detecting the state of the electronic device includes obtaining an indication of one or more of:
    (i) a 3-dimensional coordinate of a current location of the electronic device,
    (ii) a tilt of the electronic device,
    (iii) a vibration state of the electronic device,
    (iv) a velocity or acceleration of the electronic device,
    (v) a heat emission of the electronic device, (vi) heat emission of a display module of the electronic device,
(vii) a color displayed by one or more pixels of the display module,
(viii) ambient lighting,
(ix) a direction of movement of the electronic device.

14. The electronic device of claim 10, wherein each information's corresponding range is identified using a data structure stored in a memory of the electronic device that is associated the information's respective sensor.

15. The electronic device of claim 10, wherein the processing circuitry is further configured to:
identify a color that is displayed by one or more pixels of a display unit of the electronic device; and
generate the adjusted information based on the first information and the color that is displayed by the one or more pixels.

16. The electronic device of claim 10, wherein
the processing circuitry is further configured to:
receive a second information obtained from a third hardware unit; and
generate the adjusted information based on the first information, the second information, and a distance between the another device and the electronic device,
wherein
the third hardware unit is part of another device connected to the electronic device via a communications network.

17. The electronic device of claim 10, wherein the processing circuitry is further configured to:
detect the state of the electronic device includes detecting a brightness level of a display unit of the electronic device; and
generate the adjusted information based on the first information and the brightness level of the display unit.

18. The electronic device of claim 17, wherein:
the adjusted information is set to a first value when the brightness level is below a threshold; and
the adjusted information is set to a second value when the brightness level is above the threshold.

* * * * *